United States Patent
Focheux et al.

(10) Patent No.: US 6,413,532 B1
(45) Date of Patent: Jul. 2, 2002

(54) REPELLENT PEST CONTROL SYSTEM

(75) Inventors: Catherine Focheux, Setagaya (JP); Marie Pierre Puech, Ganges (FR); Robert Killick-Kendrick; Mireille Killick-Kendrick, both of Ascot (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/446,340

(22) PCT Filed: Jun. 16, 1998

(86) PCT No.: PCT/EP98/03727

§ 371 (c)(1), (2), (4) Date: Oct. 3, 2000

(87) PCT Pub. No.: WO98/57540

PCT Pub. Date: Dec. 23, 1998

(30) Foreign Application Priority Data

Jun. 18, 1997 (EP) .............................................. 97401390

(51) Int. Cl.[7] .............................................. A01N 25/32
(52) U.S. Cl. ........................ 424/406; 424/409; 424/411
(58) Field of Search ................................ 424/406, 409, 424/411

(56) References Cited

U.S. PATENT DOCUMENTS 5,437,869 A * 8/1995 Kelley ........................ 424/406

OTHER PUBLICATIONS

B. Alexander et al., "Evaluation of deltamethrin–impregnated bednets and curtains against phlebotomine sandflies . . . ", Medical and Veterinary Entomology, vol. 9, pp. 279–283 (1995).*

Killick–Kendrick et al. "Protection . . . Leishmaniasis", Medical and Veterinary Entomology, vol. 11, No. 2, pp. 105–111, (1997).*

Killick–Kendrick et al, "Protection . . . Leishmaniasis", Medical and Veterinary Entomology, vol. 11, No. 2, Apr. 1997 pp. 105–111*.

Xiong et al, "Studies . . . Transmission", Chinese Journal of Parasitology and Parasitic Diseases, vol. 13, No. 3, 1995 pp. 178–181*.

* cited by examiner

*Primary Examiner*—Alton Pryor
*Assistant Examiner*—Robert M DeWitty
(74) *Attorney, Agent, or Firm*—William P. Ramey, III

(57) ABSTRACT

A repellent solid pest control system which includes a polymeric matrix, a liquid plasticizer, a pest control active ingredient and triphenyl phosphate as a carrier for the active ingredient. Protection of dogs from bites of phlebotomine sandflies by using systems according to the inventor for the control of canine leishmaniasis.

10 Claims, No Drawings

REPELLENT PEST CONTROL SYSTEM

This application is a 371 of PCT/EP98/03727 filed Jun. 16, 1998.

The invention relates to a repellent pest control system.

A subject of the invention is a repellent pest control system for the controlled release of a pest control active ingredient from a polymer matrix which comprises
- a vinyl polymer
- a liquid plasticizer for said polymer, said plasticizer being present in the maximum amount possible and still maintain a dry and flowable blend of plasticizer and polymer and
- triphenyl phosphate, said triphenyl phosphate being present in an amount sufficient to serve as a carrier for said active ingredient.

In particular a subject of the invention is a system wherein the polymer is a vinyl chloride polymer or copolymer, and/or a system wherein the liquid plasticizer is an adipic ester or a phthalic ester, and/or a system wherein the amount of triphenyl phosphate is within the range of about 10 to 35 percent by weight of the total system.

The pest system may be produced as described in the Europeen Patent Application 539295.

As a preferred system, it can be mentioned in a solid polymeric composition for the release of a pest control active ingredient which comprises a vinyl polymer, a liquid plasticize and a pest control active ingredient, the improvement which comprises including triphenyl phosphate in said composition, said triphenyl phosphate being present in an amount sufficient to serve as a carrier for said active ingredient and precisely a composition wherein the amount of triphenyl phosphate is from about 10 to 35 percent by weight of the composition.

A more particular subject of the invention is the system wherein the active ingredient is pyrethroid.

The pyrethroid may be chosen from the following compounds: deltamethrin, acrinathrin, tralomethrin, permethrin, cypermethrin, alphamethrin, cyhalothrin, fenvalerate, cyfluthrin, flucythrin, flucythrinate, fluvalinate, fenpropathrin, bifenthrin, esfenvalerate, alphacypermethrin, betacyfluthrin, lambdacyalothrin, taufluvalinate or silafluofen.

As preferred pyrethroid, it can be mentioned deltamethrin.

The repellent system according to the invention enables external parasites to be combatted; it is applicable, in particular, to the control of acaridae, for example, ticks and scabies, the warble, insects such as lice, bugs and different kinds of biting and stinging flies.

A more particular subject of the invention is a repellent pest control system wherein the pests are phlebotomine sandflies.

Canine leishmaniasis caused by Leishmania infantum is highly prevalent in all countries of the Mediterranean subregion and in many countries of Latin America, notably Brazil. In most foci it is probable that all dogs are bitten by an infected sandfly in the first transmission season. After an incubation period of up to one year, or even more, some dogs develop clinical signs of leishmaniasis and rising titres of antibodies, whereas others mount an effective cell mediated immune response with low or negative titres of antibodies, and no signs of disease. The prevalence rates of serologically positive dogs in the Mediterranean subregion are commonly around 10% but may exceed 30%. In southern Spain, half of the dogs seen by veterinarians have leishmaniasis. Once signs of the disease are apparent, untreated dogs invariably die. Treatment (for example with pentavalent antimonials) is expensive and is almost always followed by a relapse. No vaccines are available.

The importance of canine leishmaniasis as a veterinary problem is overshadowed by the fact that dogs are reservoirs of visceral leishmaniasis for the human population and attempts to control canine leishmaniasis seem always to be aimed at reducing the risk of infection to man rather than dogs. However, with the exception of western,China where canine leishmaniasis and the human disease were eradicated by the destruction of all dogs, the results of control campaigns have been disappointing. As the vectors are not strongly endophagic (feeding indoors) or endophilic (resting indoors), insecticide spraying or houses will not greatly decrease the risk of infection, and expensive campaigns to reduce the reservoir of infection by culling seologically positive dogs have met with owner resistance and only limited success.

Among the proven or suspected vector of canine leishmaniasis in the Mediterranean subregion are *Phlebotomus perniciosus* (France, Spain, Portugal, Maghreb), *P. ariasi* (France, Spain, Portugal, Morocco), *P. perfiliewi* (Italy, Greece, Serbia, Magreb), *P. tobbi* (Greece, Cyprus, Syria), *P. neglectus* (Greece), *P. syriacus* (Syria, Lebanon, Israel) and *P. langeroni* (Egypt). These closely related flies have a similar biology. The female flies (but not the males) take blood meals from any available mammal, with a preference for canids. They bite at night the highest activity outside. The risk of infection is, therefore, somewhat higher outdoors than indoors.

In Central and South America, the closely related parasite (Leishmania chagasi) is carried by different species of sandflies (principally Lutzomyia longipalpis, but also Lu. evansi in parts of Colombia and Venezuela). As in the Mediterranean subregion, dogs are commonly infected, but the prevalence of the human disease is generally higher, notably in Brazil. The principal vector in the Neotropics is present in enormous numbers in and around houses and feeds on any available mammal or bird. It has a wide distribution and has proved impossible to control.

As a prefered subject of the invention, the repellent pest control system is a dog collar, for example a dog collar comprising 2 to 6 g of deltamethrin per 100 g of collar with an optimum of 4 g of deltamethrin per 100 g of collar.

Another subject of the invention is the protection of dog from bites of phlebotomine sandflies by deltamethrin collar for the control of canine leishmaniasis.

Deltamethrin dog collars protect dogs from almost all the bites of phlebotomine sandflies for a period up to and including 34 weeks. While absolute protection from leishmaniasis cannot be expected, the risk to dogs wearing collars should be reduced to a negligible level compared to dogs without collars. In addition, when confined with collared dogs, a high proportion of flies die within two hours. It is concluded that the collars have strong anti-feeding and lethal effects to phlebotomine sandflies lasting for a complete sandfly season.

The collars could be used in two ways. Firstly, they offer a means for owners to protect their dogs from canine leishmaniasis. secondly, they provide a unique tool in the control of human visceral leishmaniasis with dogs as the main source of infection. Because the collars break the contact between dogs and sandflies, it is probable that their universal use would stop the circulation of the parasite and the human disease would disappear.

The following examples illustrate the invention and show how it can be implemented.

EXAMPLE 1

Dog collars were made from the following formulation (percent by weight)

| | |
|---|---|
| PVC (med. mol. wt.) | 40.6 |
| Stabilizer (CZ19A) | 0.4 |
| Epoxidized oil | 5.0 |
| Dioctyl adipate | 18.0 |
| Triphenyl phosphate | 32.0 |
| Deltamethrin | 4.0 |

EXAMPLE 2

With an average metric mass of 0.390 g/cm., a collar cut to 48 cm weighs 18.72 g. For simplification purposes this weight is rounded off to 19 g. Considering that the concentration of deltamethrin in the collar is 40 mg/g then the unit formulae are the following.

| Name of ingredient | Unit formula for collar |
|---|---|
| Deltamethrin | 0.760 g |
| Organo Ca—Zn soap blend | 0.095 g |
| Epoxidized soya bean oil | 0.950 g |
| Diisooctyl adipate | 3.420 g |
| Triphenyl phosphate | 5.890 g |
| Titanium dioxide | 0.285 g |
| Polyvinyl chloride q.s. | 19.000 g |

Materials and methods

Dog collars, consisted of a 48 cm strip of polyvinyl chloride (PVC) weighing 20 g impregnated with deltamethrin 40 mg/g.

Experimental procedure, 1, 2, 3, 4, 13, 20, 26 and 34 weeks after attachment of deltamethrin-impregnated collars, two experimental dogs were sedated and put inside separate nets for 2 h with 160–200 female (and about 25 male) sand-flies, Phlebotomus perniciosus. Two other dogs without collars were similarly exposed as controls. At the end of the 2 h exposure period the dogs were removed and all dead flies were collected, kept at room temperature until the following day (in case they recovered after knock-down) and then counted, examined with a dissecting microscope and recorded as engorged or unengorged. Live flies were collected and maintained for ~20 h at 19–24° C. in suspended gauze 16 cm cubic cages, to allow for the possibility that some flies with the collared dogs might have received a low dose of insecticide causing delayed mortality. After the holding period, they were scored as either (i) live and engorged, (ii) live and unengorged, (iii) dead and engorged, or (iv) dead and inengorged.

Dogs, identified by tattooed numbers, were female laboratory bred beagles aged 7 months when the experiments started. Five collared dogs were separately housed outside in large enclosures with kennel shelters. Two control dogs without collars were similarly housed together in another outside enclosure, 25 m from the collared dogs. To ensure there was no variation in the responses of the dogs to sandfly bites that could disturb the flies, they were all sedated before each experiment with Ketamine® and Dormitor® (SmithKline Beecham) given intravenously as a mixture of 0.6–0.9 ml of each drug per 10 kg body weight (depending on the animal's reaction on a previous occasion). At these doses, sedation was satisfactory for the whole 2 h period of exposure.

Sandflies were from a closed laboratory colony of Phlebotomus perniciosus originating from Spain. The age of sandflies put into nets with dogs was 7–15 days, i.e. the age when it was found that females of this species feed most readily in the conditions of the experiments. Flies of similar age were counted from stock cages (cubic 45 cm) and distributed with an aspirator into four small cages (cubic 16 cm). They were transferred to the nets 15–30 min before the experiments. Any flies dead in the small cages were counted and the number deducted from the total. When opening the zip fasteners at the bottom of the nets to put in and take out dogs, or recapture the flies, lights were put on to attract the flies to the top of the nets. As the dogs were taken out at the end of the exposure, they were examined for dead or feeding flies (which were seldom present). The people who entered the nets to recover the flies wore overalls to prevent bites.

Results

Anti-feeding effects of the sandflies recaptured from tests 2–34 weeks after the dogs began wearing deltamethrin-impregnated collars, were demonstrated by the fact that 1911 females had engorged on the collarless (control) dogs and 75 on the dogs with collars.

More than 70% of female flies engorged on the control dogs at weeks 2–34 compared to <13% on the collared dogs.

Lethal effect. For sandflies exposed to the dogs 1 week after collars were fitted, before the insecticide from the collars had diffused well over the fur pelt of the dogs, the mortality-rate of sandflies following 2 h exposure was, as expected, the lowest (21% and 25%). From tests in weeks 2–34 the proportions of P. perniciosus dead in nets with collared dogs were 25–64%, consistently highly significantly greater than 1.1–12.0% dead in nets with collarless (control) dogs. For each pair of replicate dogs, there was no statistically significant difference in the proportions of flies dead in the nets at the end of 2 h confinement.

Overall mortality of sandflies was <16% with control dogs and >45% with collared dogs.

What is claimed is:

1. A method for repelling phlebotomine sandflies from a dog for controlling canine leishmaniasis, comprising placing on the dog a collar for the controlled release of a pyrethroid from a polymer matrix, wherein the polymer matrix comprises:

a pyrethroid, a vinyl polymer, a liquid plasticizer for said polymer, said plasticizer being present in the maximum amount possible but still maintaining a dry and flowable blend of said plasticizer and said polymer, and triphenyl phosphate being present in an amount sufficient to serve as a carrier for the pyrethroid whereby said method repells phlebotomine sandflies and controls canine leishmaniasis.

2. The method according to claim 1, wherein the polymer is a vinyl chloride polymer or copolymer.

3. The method according to claim 1, wherein the liquid plasticizer is an adipic ester or a phtallic ester.

4. The method according to claim 1, wherein the amount of triphenyl phosphate is within the range of about 10 to 35 percent by weight of the total system.

5. The method according to claim 1, wherein the amount of triphenyl phosphate is from about 10 to 35 percent by weight of the polymer matrix.

6. The method according to claim 1, wherein the pyrethroid is deltamethrin.

7. The method according to claim 1, wherein the dog collar comprises 2 to 6 g of deltamethrin for every 100 g of total weight.

8. A method for controlling canine leishmaniasis comprising placing on a dog a collar for the controlled release of a pyrethroid from a polymer matrix, wherein the polymer matrix comprises:

a vinyl polymer, a liquid plasticizer for said polymer, said plasticizer being present in the maximum amount possible but still maintaining a dry and flowable blend of said plasticizer and said polymer, and triphenyl phosphate, said triphenyl phosphate being present in an amount sufficient to serve as a carrier for the pyrethroid, whereby said repellent pest control system repels phlebotomine sandflies, thereby preventing the sandflies from infecting the dog with canine leishmaniasis.

9. The method of claim 8, wherein the pyrethroid is deltamethrin.

10. The method of claim 8, wherein the collar comprises 2 to 6 g of deltamethrin for every 100 g of total weight.

* * * * *